US011206966B2

(12) United States Patent
Petersen et al.

(10) Patent No.: US 11,206,966 B2
(45) Date of Patent: Dec. 28, 2021

(54) REDUCTION OF ENDOSCOPE HIGH FREQUENCY LEAKAGE CURRENT USING A COMMON-MODE CHOKE

(71) Applicant: Intuitive Surgical Operations, Inc., Sunnyvale, CA (US)

(72) Inventors: Alan W. Petersen, Cupertino, CA (US); Bryan E. Blair, Santa Clara, CA (US); Andrey Polonsky, Rochester, NY (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 676 days.

(21) Appl. No.: 16/072,115

(22) PCT Filed: Jan. 31, 2017

(86) PCT No.: PCT/US2017/015875
§ 371 (c)(1),
(2) Date: Jul. 23, 2018

(87) PCT Pub. No.: WO2017/136357
PCT Pub. Date: Aug. 10, 2017

(65) Prior Publication Data
US 2019/0029499 A1 Jan. 31, 2019

Related U.S. Application Data

(60) Provisional application No. 62/289,446, filed on Feb. 1, 2016.

(51) Int. Cl.
*A61B 1/00* (2006.01)
*H01F 17/06* (2006.01)
(Continued)

(52) U.S. Cl.
CPC ...... *A61B 1/00126* (2013.01); *A61B 1/00018* (2013.01); *A61B 1/00114* (2013.01);
(Continued)

(58) Field of Classification Search
CPC . A61B 1/00018; A61B 1/00114; H01F 17/04; H01F 27/2823
See application file for complete search history.

(56) References Cited

U.S. PATENT DOCUMENTS 6,430,437 B1   8/2002   Marro
8,634,901 B2 *  1/2014   Callahan .............. H01R 31/065
                                                 600/509
(Continued)

FOREIGN PATENT DOCUMENTS

CN   101553165 A   10/2009
CN   103781399 A    5/2014
(Continued)

OTHER PUBLICATIONS

International Search Report and Written Opinion for Application No. PCT/US2017/015875, dated May 19, 2017, 12 pages.
(Continued)

*Primary Examiner* — Matthew J Kasztejna

(57) ABSTRACT

An endoscope includes a body and a circuit board mounted within the body. A cable couples the circuit board to an imaging system. A common-mode choke is mounted within the body and is configured to electrically isolate the cable from the body at cautery frequencies. A method includes twisting a plurality of wires together to form a twisted set of wires. The twisted set of wires is wound around a core so that windings do not overlap, and so that a first winding and a last winding are separated from each other. Wires in the twisted set of wires are coupled to a plurality of wires in the cable. Also, these wires in the twisted set of wires are also coupled to the circuit board.

13 Claims, 4 Drawing Sheets

(51) Int. Cl.
    *H01F 17/04* (2006.01)
    *H01F 27/28* (2006.01)
    *H01F 17/00* (2006.01)
    *H01F 41/07* (2016.01)

(52) U.S. Cl.
    CPC ......... *A61B 1/00124* (2013.01); *H01F 17/04* (2013.01); *H01F 17/062* (2013.01); *H01F 27/2823* (2013.01); *H01F 41/07* (2016.01); *H01F 2017/0093* (2013.01)

(56) References Cited

U.S. PATENT DOCUMENTS

| | | | |
|---|---|---|---|
| 2007/0167827 A1 | 7/2007 | Masters | |
| 2013/0178924 A1* | 7/2013 | Atalar | A61N 1/05 607/116 |
| 2013/0317494 A1 | 11/2013 | Daw et al. | |
| 2014/0114130 A1 | 4/2014 | Ijichi | |
| 2015/0335230 A1* | 11/2015 | Tomatsu | H04N 5/2256 600/109 |

FOREIGN PATENT DOCUMENTS

| | | |
|---|---|---|
| EP | 0107266 A1 | 5/1984 |
| EP | 2591714 A1 | 5/2013 |
| WO | WO-2013049465 A1 | 4/2013 |

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

International Preliminary Report on Patentability for Application No. PCT/US2017/015875, dated Aug. 16, 2018, 8 pages.

Partial Supplementary European Search Report for Application No. 17748024.1, dated Jun. 18, 2019, 14 pages.

Extended European Search Report for Application No. EP17748024.1 dated Oct. 4, 2019, 10 pages.

* cited by examiner

REDUCTION OF ENDOSCOPE HIGH FREQUENCY LEAKAGE CURRENT USING A COMMON-MODE CHOKE

RELATED APPLICATIONS

This patent application is the U.S. national phase of International Patent Application No. PCT/US2017/015875, filed Jan. 31, 2017, which designated the U.S. and which claims priority to and the benefit of the filing date of U.S. Provisional Patent Application No. 62/289,446, (filed Feb. 1, 2016), each of which is incorporated by reference herein in its entirety.

BACKGROUND

Field of the Invention

The present invention relates generally to endoscopes for computer-assisted surgical system, and more particularly to minimizing unwanted cautery high frequency leakage current flow into the metal shaft of an endoscope.

Description of Related Art

Referring to FIG. 1, surgical system 100 is a computer assisted surgical system that includes an endoscopic imaging system 192, a surgeon's console 194 (master), and a patient side support system 110 (slave), all interconnected by wired (electrical or optical) or wireless connections 196. One or more electronic data processors may be variously located in these main components to provide system functionality. Examples are disclosed in U.S. Patent Application Publication No. US 2008/0065105 A1, which is incorporated by reference herein.

Patient side support system 110 includes an entry guide manipulator 130, which may also be called an actively controlled manipulator arm assembly 130. At least one surgical device assembly is coupled to entry guide manipulator 130. Each surgical device assembly includes an instrument having either a surgical instrument or an image capture unit. For example, in FIG. 1, one surgical device assembly includes an instrument 135-1 with a shaft 137-1 and an image capture unit that extends through entry guide 115 during a surgical procedure. Instrument 135-1 is sometimes referred to an endoscope, or alternatively as an imaging system device or camera instrument. Typically, entry guide 115 includes a plurality of channels.

Imaging system 192 performs image processing functions on, e.g., captured endoscopic imaging data of the surgical site and/or preoperative or real time image data from other imaging systems external to the patient. Imaging system 192 outputs processed image data (e.g., images of the surgical site, as well as relevant control and patient information) to a surgeon at surgeon's console 194. In some aspects, the processed image data is output to an optional external monitor visible to other operating room personnel or to one or more locations remote from the operating room (e.g., a surgeon at another location may monitor the video; live feed video may be used for training; etc.).

Surgeon's console 194 includes multiple degrees-of-freedom ("DOF") mechanical input devices ("masters") that allow the surgeon to manipulate the instruments, entry guide(s), and imaging system devices, which are collectively referred to as slaves. These input devices may in some aspects provide haptic feedback from the instruments and surgical device assembly components to the surgeon. Surgeon's console 194 also includes a stereoscopic video output display positioned such that images on the display are generally focused at a distance that corresponds to the surgeon's hands working behind/below the display screen. These aspects are discussed more fully in U.S. Pat. No. 6,671,581, which is incorporated by reference herein.

Control during insertion of the instruments may be accomplished, for example, by the surgeon moving the instruments presented in the image with one or both of the masters; the surgeon uses the masters to move the instrument in the image side to side and to pull the instrument towards the surgeon. The motion of the masters commands the imaging system and an associated surgical device assembly to steer towards a fixed center point on the output display and to advance inside the patient.

In one aspect, the camera control is designed to give the impression that the masters are fixed to the image so that the image moves in the same direction that the master handles are moved. This design causes the masters to be in the correct location to control the instruments when the surgeon exits from camera control, and consequently this design avoids the need to clutch (disengage), move, and declutch (engage) the masters back into position prior to beginning or resuming instrument control.

Base 101 of patient side support system 110 supports an arm assembly that includes a passive, uncontrolled setup arm assembly 120 and an actively controlled manipulator arm assembly 130. Actively controlled manipulator arm assembly 130 is sometimes referred to as entry guide manipulator 130. An entry guide manipulator assembly platform 132, sometimes referred to as platform 132, is coupled to a distal end of fourth manipulator link 119. An entry guide manipulator assembly 133 is rotatably mounted on platform 132. Arrow 190 shows the distal and proximal directions.

Entry guide manipulator assembly 133 includes an instrument manipulator positioning system. Entry guide manipulator assembly 133 rotates a plurality of instrument manipulator assemblies 140-1, 140-2 as a group around axis 125.

Each of a plurality of instrument manipulator assemblies 140-1, 14-2 is coupled to entry guide manipulator assembly 133 by a different insertion assembly 136. In one aspect, each insertion assembly 136 is a telescoping assembly that moves the corresponding instrument manipulator away from and towards entry guide manipulator assembly 135. In FIG. 1, each of the insertion assemblies is in a fully retracted position.

Each of the plurality of instrument manipulator assemblies 140-1, 140-2 includes a plurality of motors that drive a plurality of outputs in an output interface of that instrument manipulator. See U.S. Patent Application No. 61/866,115 (filed on 15 Aug. 2013), which is incorporated by reference, for one example of an instrument manipulator and a surgical instrument that can be coupled to the instrument manipulator.

Each of plurality of surgical device assemblies 180 includes a different of the plurality of instrument manipulator assemblies and one of a surgical instrument and an image capture unit. Each of instruments 135-1, 135-2 includes a body that houses a transmission unit. The transmission unit includes an input interface including a plurality of inputs. Each of instruments 135-1, 135-2 also includes a shaft 137-1, 137-2 sometimes referred to as a main tube that extends in the distal direction from the body. An end effector is coupled to a distal end of the shaft of a surgical instrument assembly, and an image capture unit, e.g., a camera, is included in a distal end of a different surgical instrument assembly. See U.S. Patent Application No. 61/866,115 (filed on 15 Aug. 2013), which is incorporated by reference, for one example of an instrument manipulator assembly and a surgical instrument.

Each of instruments 135-1, 135-2 is coupled to the instrument mount interface of a corresponding instrument manipulator assembly 140-1, 140-2 so that a plurality of inputs in an input interface of the transmission unit in instrument 135-1, 135-2 are driven by plurality of outputs in the instrument mount interface of instrument manipulator assembly 140-1, 140-2. See U.S. Patent Application No. 61/866,115 (filed on 15 Aug. 2013).

As shown in FIG. 1, the shafts of plurality of surgical device assemblies 180 extend distally from bodies of the instruments. The shafts extend through a cannula 116 placed at the entry port into the patient (e.g., through the body wall or at a natural orifice). In one aspect, an entry guide 115 is positioned within cannula 116, and each instrument shaft extends through a channel in entry guide 115, so as to provide additional support for the instrument shafts.

SUMMARY

A surgical system includes an endoscope and a cable connecting the endoscope to an imaging system. The cable including a first plurality of wires. The endoscope includes a body, a circuit board mounted within the body, and a common-mode choke mounted within the body. The common-mode choke is coupled to the first plurality of wires and is coupled to the circuit board.

The cable includes a shield that encloses, e.g., surrounds, the first plurality of wires. The shield is connected to the common-mode choke so that the common-mode choke electrically isolates the cable shield from the body of the endoscope.

In one aspect, the common-mode choke includes a second plurality of wires. The second plurality of wires includes a first end, a second end, and a portion between the first end and the second end. The portion of the second plurality of wires between the first end and the second end is wound around the core in non-overlapping windings and is wound so that the first end and the second end are separated from one another. Some of the wires of the second plurality of wires are coupled to the first plurality of wires and to the circuit board. In one aspect, the second plurality of wires are twisted together prior to being wound around the core.

In one aspect, the core of the common-mode choke is a gapless core. The gapless core is, for example, a nano-crystalline ferrite core.

In another aspect, the endoscope includes an electrical optical coupler coupled to common-mode choke and coupled to the circuit board.

In still another aspect, a method includes reducing common-mode current induced on a cable of an endoscope by coupling a common-mode choke between the cable and a circuit within the endoscope.

In yet another aspect, a method includes twisting a plurality of wires together to form a twisted set of wires. The twisted set of wires is wrapped around a core so that windings do not overlap, and so that a first winding and a last winding are separated from each other. One or more of the wires in the twisted set of wires are coupled to one or more wires in a plurality of wires of a cable of an endoscope. The one or more wires in the twisted set of wires are also coupled to a circuit board. A shield of the cable is connected to one wire of the twisted set of wires. The one wire being different from the one or wires in the twisted set of wires.

Figure 1:
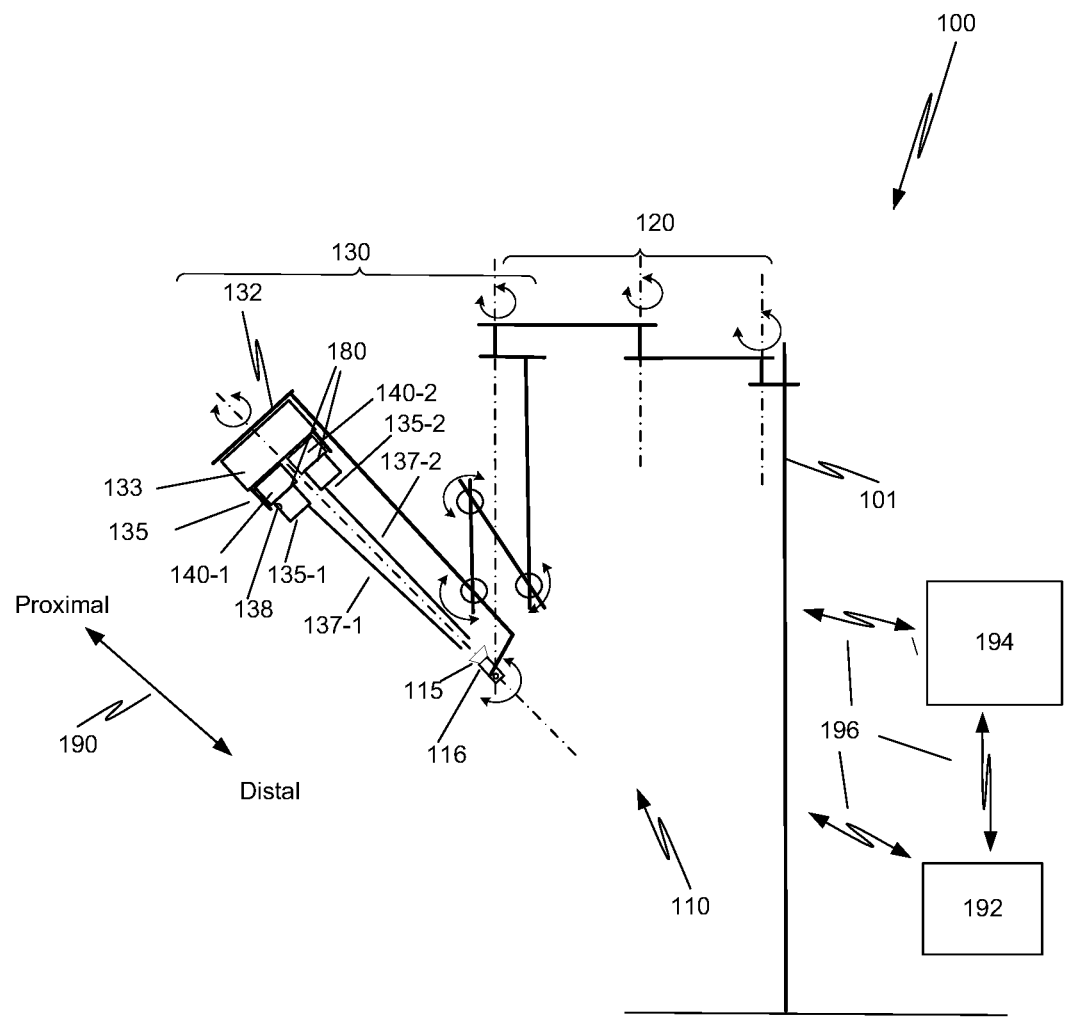
FIG. 1 is an illustration of a prior-art computer-assisted surgical system.

In the drawings, the first digit of a three digit reference numeral is the figure number in which the element having that reference numeral first appeared.

DETAILED DESCRIPTION

In surgical system 100, typically a cable runs between endoscope 135-1 and imaging system 192. The cable has a significant capacitance to ground. When one of the instruments in surgical system 100 includes or is an energized cautery tool, the cautery tool's energy source provides high frequency energy with the main energy being located in the 400 kHz to 500 kHz range and with harmonics up to the 4 MHz range. The cautery tool energy source can unintentionally supply energy to any object that has a path to ground (earth) by a direct wired connection or by capacitive coupling. The cautery tool energy source can source this energy from either of its two output leads: (1) the High Voltage lead which connects to the cautery tool or (2) the Patient Return lead normally connected to the patient's body.

The cautery tool energy source can drive current into the endoscope's metal shaft 137-1 by virtue of the shaft being electrically connected to the cable which has a large capacitance to earth. The current can travel by two paths: (1) from the cautery tool energy source High Voltage lead being capacitively coupled (wrapped around) the endoscope cable, or (2) from patient's body (which is connected to the Patient Return lead) touching the endoscope shaft. During cautery activation unintended current flow may cause arcing at the patient-tissue-endoscope-shaft interface. An arc at the patient's tissue, may burn the tissue, and of course is undesirable.

Endoscope 200 (FIG. 2) reduces the unintended current flow by inserting a high impedance component 215 (which may be high impedance at all signal frequencies, or only within a range of frequencies such as at cautery frequencies) between the endoscope body, e.g., housing 201 (sometimes referred to as body 201), and the large capacitance to ground of cable 205. This high impedance component 215 may also be called a common-mode choke 215. Cable 205 connects endoscope 200 to imaging system 292. Imaging system 292 is equivalent to imaging system 192. At the same time, in various embodiments, component 215 must not have a high impedance for the data and power wires of cable 205. In one aspect, this component is a common-mode choke 215. The data and power are differential signals (traveling down one wire and returning on it companion ground wire, whereas the cautery current tries to travel in common down all the wires). Common-mode choke 215 behaves as a high impedance for common-mode currents and as a low impedance for differential currents.

Common-mode choke 215 is included within housing 201 of endoscope 200. Common-mode choke 215 is connected between cable 205 and a circuit board 210 and connected between a shield of cable 205 and housing 201, sometimes referred to as body 201. In one aspect, common-mode choke 215 is mounted on circuit board 210. Common-mode choke 215 has an inductance in the tens of millihenries, e.g., 30 millihenries in one aspect, and so attenuates any common-mode current on cable 205 by over a factor of three. This attenuation is sufficient to reduce the common-mode cautery current to levels accepted by international standards. Common-mode choke 215 has minimal stray capacitance between its input and output leads. The signal coupling between parallel windings of common-mode choke 215 is small enough that signal integrity is not compromised.

In one aspect, endoscope 200 includes a plurality of image capture units in the distal end of main tube 202. An illuminator in endoscope 200 provides light to the distal end of main tube 202. Arrow 290 defines the proximal direction and the distal direction in FIGS. 2, 4A, and 4B.

The circuits included within housing 201 of endoscope 200 that power the illuminator and the image capture units, move data from the image capture units to imaging system 292, etc. are represented by circuit board 210. Circuit board 210, in some instances, may be implemented by more than one circuit board. Circuit board 210 is coupled to units in the distal end of main tube by a cable 203. There may be other cables that run from circuit board 210 to other elements housed within housing 201. The size and shape of housing 201 is fixed by the need for endoscope 200 to be in close proximity to other instruments, as shown in FIG. 1, and to not collide with the other instruments or inhibit the range of motion of the other instruments.

Figure 2:
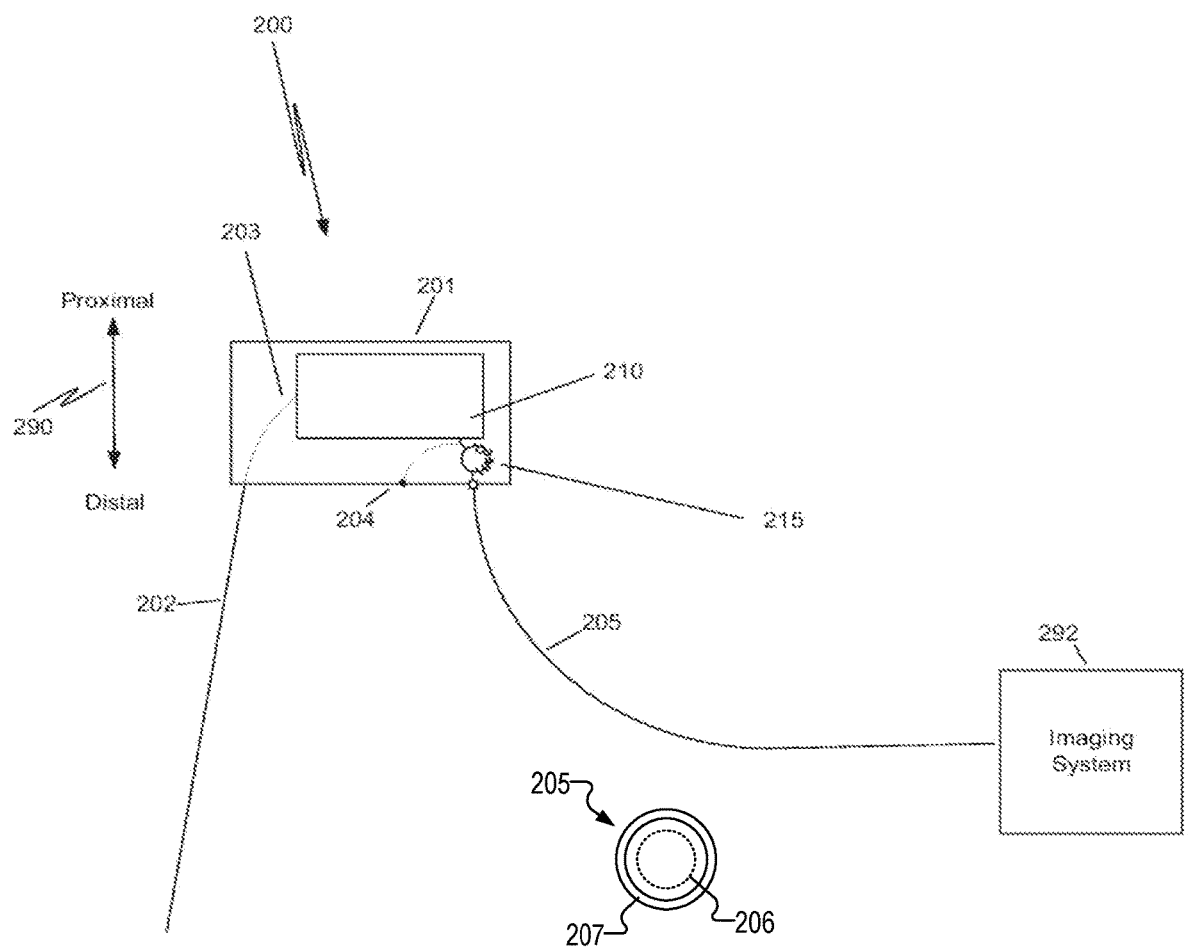
FIG. 2 is an illustration of an endoscope connected to a cable with a common-mode choke connecting the cable to the circuit board in the endoscope.

Cable 205 includes, in one aspect, a power line, a ground line, signal lines, and a shield that encloses these lines. The power line, ground line, and signal lines together are sometimes referred to as a first plurality of wires. For example, a cross-sectional view of cable 205 is shown in FIG. 2 and shows the first plurality of wires 206 (represented in FIG. 2 by a dashed circle) enclosed by a shield 207. Thus, in this aspect, the first plurality of wires is encased in a shield. Cable 205 is connected to housing 201. However, in connecting cable 205 to housing 201, neither the shield nor any of the wires in cable 205 are permitted to contact housing 201.

Common-mode choke 215 is connected to the first plurality of wires and, in this aspect, is connected to circuit board 210, i.e., is connected between cable 205 and circuit board 210. The shield of cable 205 is also connected thru common-mode choke 215 to a ground 204 on housing 201. The shield of cable 205 is electrically isolated from housing 201 of endoscope 200 by common-mode choke 215, and the shield does not touch any electrically conductive part that is connected to housing 201.

Common-mode choke 215 includes a plurality of non-overlapping windings. A beginning winding in the plurality of non-overlapping windings is separated from an ending winding of the plurality of non-overlapping windings. Since the windings of common-mode choke 215 do not overlap and the beginning winding is separated from the ending winding, there is minimal capacitance across the input and output leads of common-mode choke 215. In this aspect, the core of common-mode choke 215 does not have an opening and is selected to have the highest AL-value (number of millihenries per turn) possible for the size of the core.

Figure 3A:
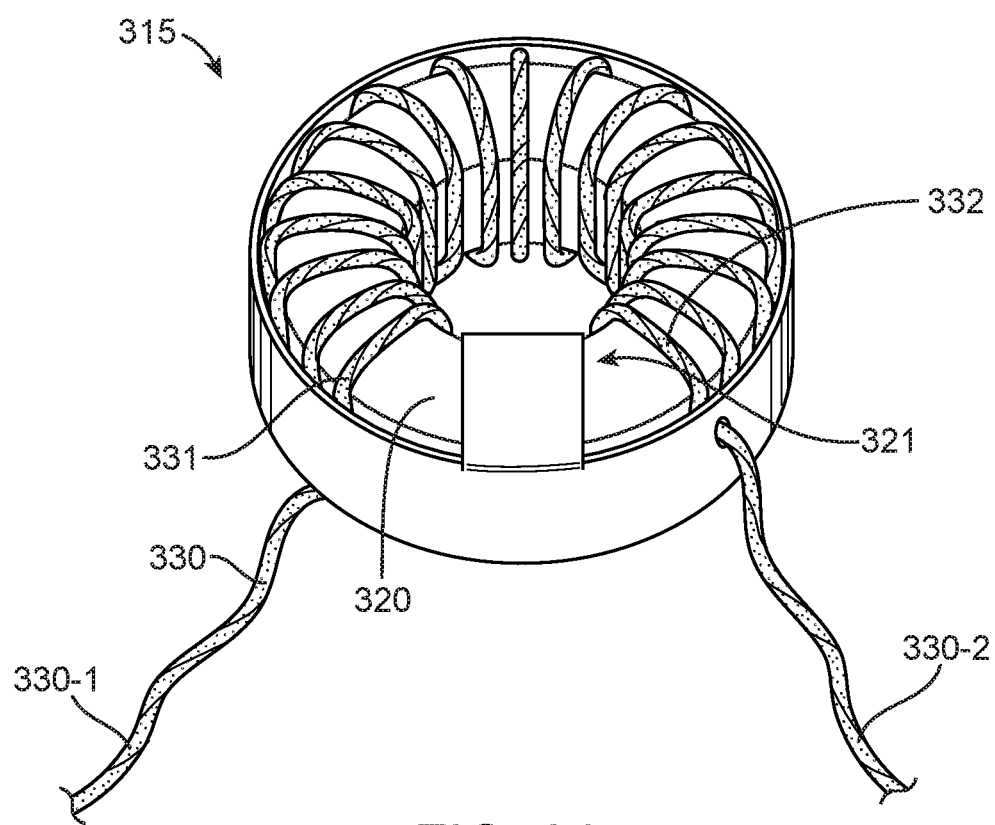
FIG. 3A is an illustration of one aspect of the common-mode choke.
Figure 3B:
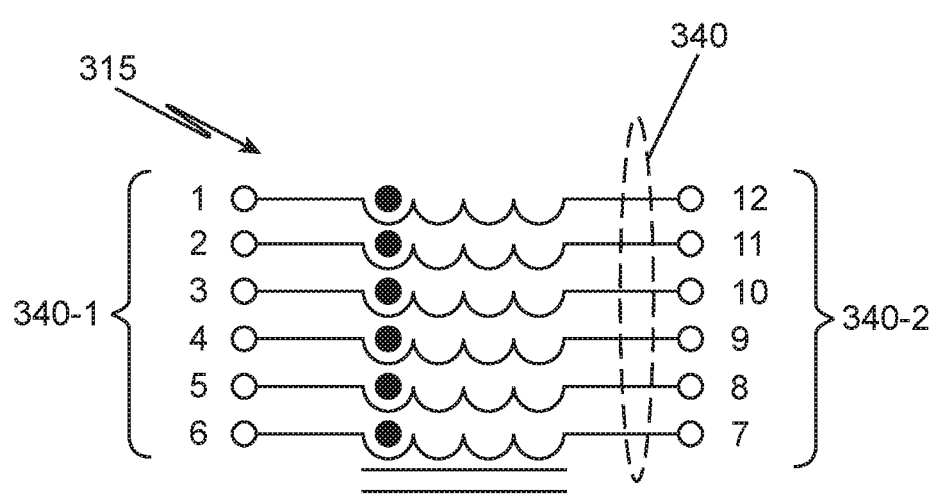
FIG. 3B is a schematic diagram of the common-mode choke.

FIG. 3A is an illustration of common-choke 315, an embodiment of common-mode choke 215. FIG. 3B is a schematic diagram of common-mode choke 315. In this aspect, cable 205 includes a ground line, a power line, four signal lines and the shield surrounding these lines. After cable 205 enters housing 201, the ground line and the shield are twisted together so that there are six lines, a shield and ground line combination, a power line, and four signal lines.

Common-mode choke 315 includes a second plurality of wires 340, which in this example, is six wires. Prior to being wound on core 320, second plurality of wires 340 are twisted together to form a set of twisted wires 330. Set of twisted wires 330 has a first lead 330-1, a second lead 330-2, and a portion between first lead 330-1 and second lead 330-2. Similarly, each wire of the second plurality of wires 340 has a first end 340-1, a second end 340-2 and a portion between first end 340-1 and second end 340-2.

Set of twisted wires 330, sometime referred to as wires 330, are wound around core 320 so that the windings do not overlap. Avoiding overlap of the windings has several advantages. There is minimal capacitance created between winding, and this helps to minimize the input-to-output capacitance of common-mode choke 315.

Since there are no overlapping windings, there is no concern about arcing between overlapping windings due to insulation failure. In one aspect, the common-mode voltage is about 3000 volts, and, in this aspect, common-mode choke 315 has 28 windings. Thus, each winding drops around 107 volts, which is well within the capability of conventional wire insulation. Thus, the non-overlapping windings eliminate any concern about the insulation on wires 330 failing.

A first winding 331, a beginning winding, around core 320 is separated by a gap 321 from a last winding 332, an ending winding, around core 320. Gap 321 separates input lead 330-1, a first lead, from output lead 330-2, a second lead, which also helps to minimize the capacitance of common-mode choke 315 and also helps to prevent arching between the first lead and second lead. As shown in FIG. 3A, the windings around core 320 have a letter "C" shape, where gap 321 in the windings is the opening in the letter "C" shape. The size of gap 321 is selected so that there is no possibility of arcing between input lead 330-1 and output lead 330-2.

Core 320 is a ferrite toroid core or a ferrite bobbin/pot core. In one aspect, core 320 is a nano-crystalline ferrite core without a gap. This core material provides a much higher inductance per turn compared to other core materials, which results in less stray capacitance from input lead 330-1 to output lead 330-2. In one aspect, core 320 is a nano-crystalline ferrite core in a plastic casing. This core has properties such as those in Table 1.

TABLE 1

| Nominal Core Dimensions | | |
|---|---|---|
| Outer Diameter | | 16 mm |
| Inner Diameter | | 10 mm |
| Height | | 6 mm |
| Iron Cross Section | | |
| $A_{Fe}$ | | 0.14 cm$^2$ |
| | AL | |
| 10 KHz | | 43.0 µH |
| 100 kHz | | 10.1 µH |

TABLE 1-continued

Saturation Current $I_{cm}$

| | |
|---|---|
| 10 KHz | 0.3 A |
| 100 kHz | 0.6 A |

A core having these properties is commercially available from Vacuumschmelze GMBH & Co., Gruner Weg 37, D 63450 Hanau, Germany under Part No. T6006-L2016-W403. While the dimensions of the core are given in Table 1, the cross sectional area of the core is a key factor in setting the maximum current the core can handle before the core saturates (where the inductance droops to a lower value). Another core choice with different dimensions is just as effective if that core has approximately the same AL value and cross-sectional area.

Each of the six wires in the twisted set of wires in input lead 330-1 of common-mode choke 315 are either connected to (FIGS. 2 and 4A) or are coupled to (FIG. 4B) a different one of the six wires (a shield and ground line combination, a power line, and four signal lines) of cable 205. Thus, each of the six wires—an example of a plurality of wires—in the twisted set of wires in input lead 330-1 are coupled to a different one of the six wires (a shield and ground line combination, a power line, and four signal lines) of cable 205.

One of the six wires in the twisted set of wires in output lead 330-2 of common-mode choke 315—the one coupled to the a shield and ground line combination of cable 205—is connected to a ground 204. The other wires in the six wires in the twisted set of wires in output lead 330-2 of common-mode choke 315 are coupled to circuit board 210.

While in this aspect, a gapless nano-crystalline ferrite is used, in other aspects, a gapless ferrite core could be used if the performance characteristics of the gapless ferrite core are acceptable for the common mode currents encountered during a surgical procedure and if there is space for the resulting common-mode choke within the instrument. Similarly, a gapped ferrite core could be used if the performance characteristics of the gapped ferrite core are acceptable for the common mode currents encountered during a surgical procedure and if there is space for the resulting common-mode choke within the instrument.

Electrical optical couplers have been considered in electrically isolating cable 205 from housing 201 of endoscope 400A. Typically, an electrical optical coupler functions properly so long as the common-mode voltages are less than about 25,000 volts/microsecond. With an arcing cautery instrument, a typical voltage is 3000 volts, and the rise time of the arc is on the order of five to ten nanoseconds, which results in about 500,000 volts/microsecond. Hence, an electrical optical coupler alone would not work properly in the presence of common-mode voltages generated by an arcing cautery instrument. However, a common-mode choke combined with an electrical optical coupler attenuates the common-mode voltage so that the electrical optical coupler works properly.

Figure 4A:
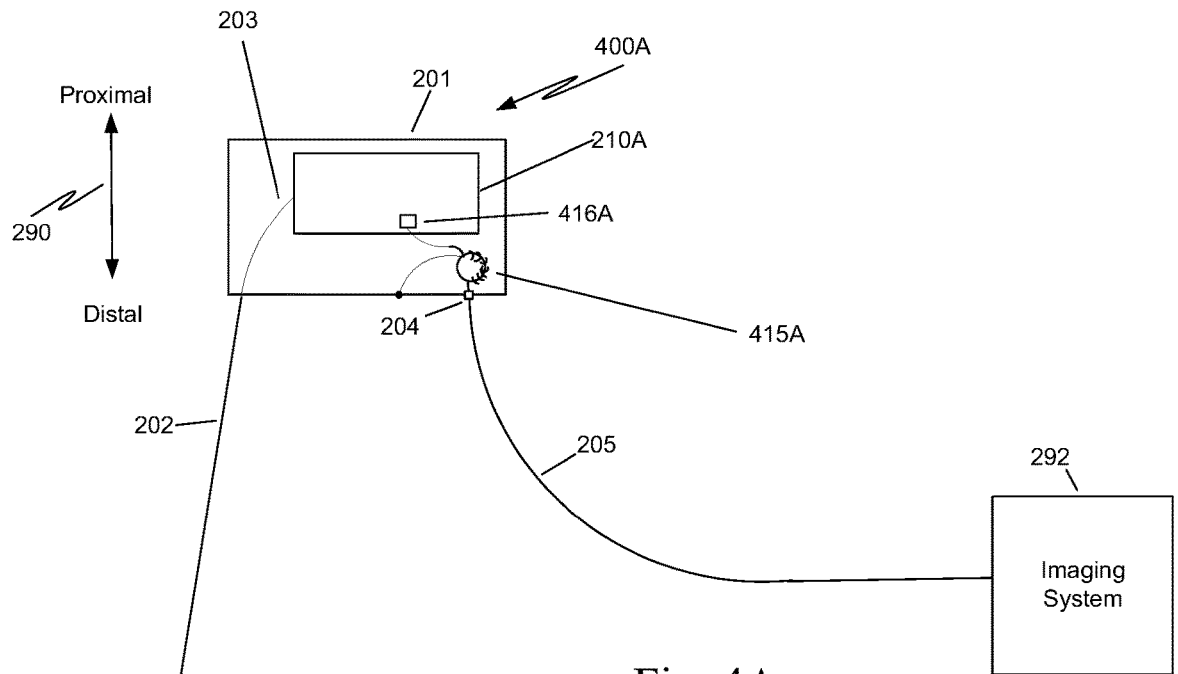
FIGS. 4A and 4B are each an illustration of another endoscope connected to a cable with a combination of a common-mode choke and an electrical optical coupler.
Figure 4B:
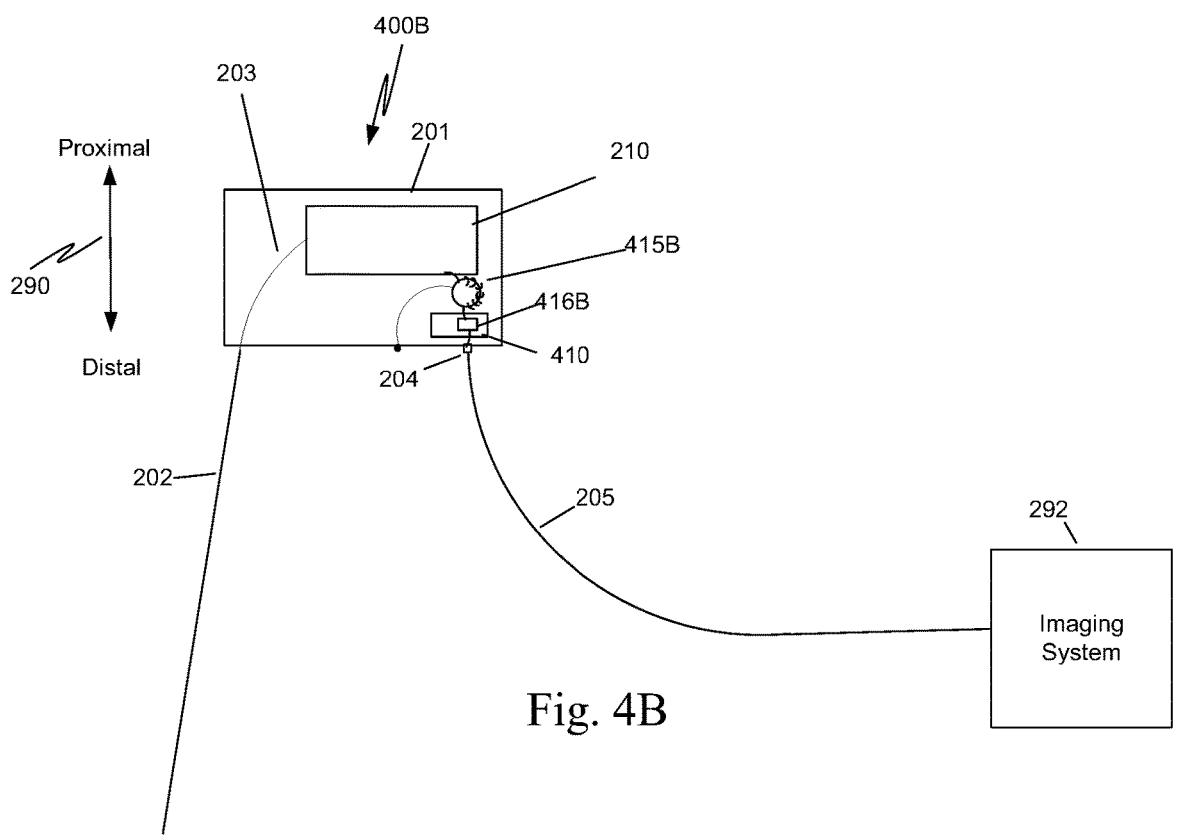

FIGS. 4A and 4B illustrate two equivalent ways of utilizing a common-mode choke with an optical coupler. In FIG. 4A, common-mode choke 415A is inserted between an electrical optical coupler 416A on circuit board 210A and cable 205. In one aspect, common mode choke 415A is also mounted on circuit board 210A. In FIG. 4B, electrical optical coupler 416B is on a circuit board 410 and cable 205 is connected to optical coupler 416B. Common mode choke 415B is connected between electrical optical coupler 416B and circuit board 210.

Common-mode chokes 415A and 415B are constructed in a way that is equivalent to the way that common-mode choke 215 was constructed, except common-mode chokes 415A and 415B are each smaller than common-mode choke 215. While common-mode choke 215 has an inductance in the tens of millihenries, each of common-mode chokes 415A and 415B has an inductance of about 100 microhenries. This means that a smaller core and a smaller number of windings can be used. However, the windings still do not overlap and the first winding is separated from the last winding so that the windings have the letter "C" shape. The other aspects of common-mode chokes 415A and 415B are the same as common-mode choke 215, and so are not repeated here.

As used herein, "first," "second," "third," etc. are adjectives used to distinguish between different components or elements. Thus, "first," "second," and "third" are not intended to imply any ordering of the components or elements or to imply any total number of components or elements.

The above description and the accompanying drawings that illustrate aspects and embodiments of the present inventions should not be taken as limiting—the claims define the protected inventions. Various mechanical, compositional, structural, electrical, and operational changes may be made without departing from the spirit and scope of this description and the claims. In some instances, well-known circuits, structures, and techniques have not been shown or described in detail to avoid obscuring the invention.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of the device in use or operation in addition to the position and orientation shown in the figures. For example, if the device in the figures were turned over, elements described as "below" or "beneath" other elements or features would then be "above" or "over" the other elements or features. Thus, the exemplary term "below" can encompass both positions and orientations of above and below. The device may be otherwise oriented (rotated 90 degrees or at other orientations) and the spatially relative descriptors used herein interpreted accordingly. Likewise, descriptions of movement along and around various axes include various special device positions and orientations.

The singular forms "a", "an", and "the" are intended to include the plural forms as well, unless the context indicates otherwise. The terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

All examples and illustrative references are non-limiting and should not be used to limit the claims to specific implementations and embodiments described herein and their equivalents. Any headings are solely for formatting and should not be used to limit the subject matter in any way, because text under one heading may cross reference or apply to text under one or more headings. Finally, in view of this disclosure, particular features described in relation to one aspect or embodiment may be applied to other disclosed aspects or embodiments of the invention, even though not specifically shown in the drawings or described in the text.

Embodiments described above illustrate but do not limit the disclosure. It should also be understood that numerous modifications and variations are possible in accordance with the principles of the present disclosure. For example, in many aspects the devices described herein are used as single-port devices; i.e., all components necessary to complete a surgical procedure enter the body via a single entry port. In some aspects, however, multiple devices and ports may be used.

We claim:

1. An imaging apparatus comprising:
a cable, an imaging system, and an endoscope;
the cable being configured to be connected to the imaging system and to the endoscope;
the cable including a first plurality of wires and a shield enclosing the first plurality of wires; and
the endoscope being configured to be connected to the cable, the endoscope comprising:
a body;
a circuit board mounted within the body; and
a common-mode choke mounted in the body and configured to attenuate any common-mode current on the cable, the common-mode choke being coupled to the first plurality of wires and to the shield, the common-mode choke connecting the first plurality of wires to the circuit board and the shield to a ground of the body.

2. The apparatus of claim 1, wherein the shield is electrically isolated from the body by the common-mode choke.

3. The apparatus of claim 1, the common-mode choke having a first winding and a last winding, the first winding not overlapping with and separated from the last winding.

4. The apparatus of claim 1, the common-mode choke having a plurality of non-overlapping windings.

5. The apparatus of claim 4, the plurality of non-overlapping windings including a first winding and a last winding, the first winding not overlapping with and separated from the last winding.

6. The apparatus of claim 1, the common-mode choke having a second plurality of wires and a core, the second plurality of wires having a first end and a second end, a portion of the second plurality of wires between the first end and second end being wound around the core in non-overlapping windings and being wound so that the first end and the second end are separated from one another, wherein wires of the second plurality of wires are coupled to the first plurality of wires and to the circuit board.

7. The apparatus of claim 6, the second plurality of wires being twisted together prior to being wound around the core.

8. The apparatus of claim 6, the cable further comprising a shield, the first plurality of wires being enclosed in the shield, the shield being coupled to a wire of the second plurality of wires.

9. The apparatus of claim 6, the core being a gapless core.

10. The apparatus of claim 9, the core being a nano-crystalline ferrite core.

11. The apparatus of claim 6, the core being a nano-crystalline ferrite core.

12. The apparatus of claim 6, wherein the core is a gapless, nano-crystalline ferrite core.

13. The apparatus of claim 1, the endoscope further comprising an electrical optical coupler coupled to the cable and coupled to the common-mode choke.

* * * * *